(12) United States Patent
Sangwan et al.

(10) Patent No.: US 6,586,248 B2
(45) Date of Patent: Jul. 1, 2003

(54) PROCESS FOR THE INDUCTION OF NORMAL ROOTS ON NODES AND INTERNODES OF STEM SEGMENTS WITHOUT USING HORMONE AND/OR CHEMICAL TREATMENTS IN MENTHA SPECIES

(75) Inventors: Rajender Singh Sangwan, Lucknow (IN); Neelam Singh Sangwan, Lucknow (IN); Sushil Kumar, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/258,883

(22) Filed: Mar. 1, 1999

(65) Prior Publication Data

US 2002/0168770 A1 Nov. 14, 2002

Related U.S. Application Data

(63) Continuation of application No. 09/258,883, filed on Mar. 1, 1999.

(30) Foreign Application Priority Data

Feb. 12, 1999 (IN) .................................................. 241/99

(51) Int. Cl.$^7$ ................................................ C12N 5/00
(52) U.S. Cl. ...................... 435/420; 435/430; 435/410; 47/59 R
(58) Field of Search ................................ 435/420, 430, 435/410

(56) References Cited

U.S. PATENT DOCUMENTS 4,763,442 A * 8/1988 Saeger ........................... 47/63

OTHER PUBLICATIONS

Baylis, Maggie, 1973, *House Plants for the Purple Thumb*, pp. 125–127.*
Harris, Dudley, 1988, *Hydroponics*, pp. 24–26 and 163–165.*
von Hentig, Wolf–Uwe, 1986, Rooting Temperatures of Ornamental Cuttings for Hydroculture Systems Abs 847.*
Langer, Richard W., 1975, *Grow it Indoors*, pp. 288–290.*
Mason, et al., 1990, *Commericial Hydroponics*, p. 155.*
Resh, Howard M., 1989, *Hydroponic Food Production*, pp. 110–111 and 347–348.*
Schafer–Menuhr, A, 1985, *In Vitro Techniques*, pp. 60–61.*
Wickremesinhe, Enaksha R.M., 1994, Roots of hydroponically grown *Taxus* plants as a source of taxol and related taxanes, p. 126.*
Taji et al., 1989, In Vitro Propagation of *Clianthus–Formosus* Sturt's Desert Pea an Australian Native Legume, pp. 61–66.*
Wang, Q. C., 1992, The effect of light, darkness and temperature on micropropagation of the pear rootstock BP10030, pp. 860–876.*
Rech et al., 1986, Tissue culture propagation of *Mentha* spp. by the use of axillary buds, Plant Cell Reports, pp. 17–18.*
DeBaggio, Thomas, Growing Herbs From Seed, Cutting & Root, 1994, Interweave Press, Inc. pp. 39–42.*
California Agricultural Education, Vegetative cuttings (CLF6255), 1992, pp. 1–3.*
M. Nishigori, JP 7–222536 (Abstract), "Shooting from Shoot Primordium Derived From Embryo of First Filial Generation F1 of Larix Gmelini Ledeb", 8/95.
E.R.M. Wickremesinhe et al., "Roots of hydroponically grown *Taxus* plants as a source of taxol and related taxanes", Plant Science 101:125–135, 1994.
S. Banerjee et al., "Hairy roots in medicinal plants", Curr. Res. Med. Aromatic Plants, 17:348–377, 1995.
O. Faure et al., "Mannitol and thidiazuron improve in vitro regeneration from spearmint and peppermint leaf disks", Plant Cell, Tissue and Organ Culture, 52:209–212, 1998.
S. Krasnyanski et al., "Somatic hybridization in mint: identification and characterization of *Mentha piperita* (+) *M. spicata* hybrid plants", Theor. Appl. Genet., 96:683–687, 1998.
A.K. Kukreja et al., "Genetic Improvement of Mints: On the . . . Derived Clones of Japanese Mint", J. Essent. Oil Res., 4:623–629, 1992.
A.K. Kukreja et al., "Screening and evaluation of agronomically useful somaclonal variations in Japanese mint", Euphytica 53:183–191, 1991.
C.S. Rao et al., "Protocol for in vitro propagation of *Excoecaria agallocha* L., a medicinally important mangrove species", Plant Cell Reports, 17:861–865, 1998.

* cited by examiner

Primary Examiner—Bruce R. Campell
Assistant Examiner—June Hwu
(74) Attorney, Agent, or Firm—Foley & Lardner

(57) ABSTRACT

The invention provides a process for the induction of normal rooting on nodal and internodal stem segments without using hormones and/or other chemical treatments in Mentha species, which comprises oblique excision of shoots of Mentha species from the plants, immediately dipping the cut end of twigs or stems into water and keeping in complete dark for up to one week with by varying the temperature cycle for each set of 24 hours duration of the treatment.

13 Claims, No Drawings

US 6,586,248 B2

PROCESS FOR THE INDUCTION OF NORMAL ROOTS ON NODES AND INTERNODES OF STEM SEGMENTS WITHOUT USING HORMONE AND/OR CHEMICAL TREATMENTS IN MENTHA SPECIES

This is a Continuation Application of U.S. application Ser. No. 09/258,883, filed Mar. 1, 1999, which is incorporated herein by reference in its entirety.

FIELD OF INVENTION

The present invention relates to a process for the induction of normal rooting on nodal and internodal stem segments without using hormones and/or other chemical treatments in Mentha species. The invention more particularly provides a new and easy system of inducing normal roots on plant cuttings thereby leading to large scale production of propagules ready for field plantation of mints (Mentha species).

BACKGROUND OF INVENTION

Mentha species, constitute not only the major essential oil crops of global significance but also serve as some of the chief culinary herbs. The essential oils extracted from the herb biomass is extracted through hydro-distillation. The volatile oil is a complex mixture of mainly monoterpenoids. The oils per se or their specific constituents find extensive use in a large cosmetic and pharmaceutical industries all over the world. Some of the highly functionalized monoterpenoidal constituents of the oil serve as novel synthagens for various chemcial industries. Different Mentha species serve as source of one or more of the popular natural phytochemicals like menthol, linalool, linalyl acetate, carvone, menthone etc. The ever increasing demand and utility of the oils or their specific constituents from the impetus of their increased significance as crops of choice for profitable agro-business. Furthermore, some of the species are as such consumed as ingredients of foods, spices and culinary herbal formulations etc. like *Mentha piperita, Mentha virdis* etc.

Many commercial Mentha species (e.g. *Mentha arvensis, Mentha piperita*) are propagated from subterranean suckers, stolons, etc. An area, preferably pertaining to the best land, of the previous crop is saved after second harvest (August) which during winter period produce underground suckers. In practice, in the months of January and February i.e., ending winters, the suckers are dug out, cut into about one inch pieces and directly planted in to the field and the new crop is irrigated immediately. The suckers thus sown take about 18 to 30 days to sprout (Kumar et al. 1997, CIMAP—Farm Bulletin Number 004). However, the 'above ground canopy' of the sucker-crop remains useless. It has never been explored for development of propagules concurrently for the new crop plantation. Thus, no state of the art already exists concerning the utilization and development of the aerial plant canopy as propagules for the plantation.

Rooting in mints and other plants under in vitro conditions is known to be induced by hormonal (auxins, IAA, IBA, NAA, BA, gibbrellins, cytokinin etc.) treatment and/or under culture media (e.g. MS medium, Murashige et al. 1962, Physiol. Plant. 15:473–497; LS medium, Linsmayer and Skoog 1965, Physiol. Plant 18:100–127) consisting of a number of ingredients including anions, cations, carbohydrates, nitrogenous compounds, vitamins, and singal metabolites like $Ca^{2+}$, inositols etc. (Kukreja et al., 1991 J. Essential Oil Res. 4:623–629; Kukreja et al. 1992 Euphytica 53:183–192; Faure et al. 1998, Plant Cell Tissue and Organ Culture 52:204–212; Krasnyanski et al. 1998, Theor.App. Genet. 96:683–687, Rao et al. 1998, Plant Cell Rep. 17:861–865). The rooting in dicots, may also be induced by infective method i.e., with the help of *Agrobacterium rhizogenes*. However, the roots (so called 'hairy roots') so obtained are not physiologically and genetically normal and native and behave differently (Banerjee et al., 1995, Curr. Res. Med. Aromatic Plants 17:348–378). Rooting in plant shoots and twigs have also been propagated under defined nutrient solutions like Hoagland Solutions, Johnsons Nutrient Solutions of various concentration-strengths have been used for long-term plant maintenance hydroponically and for root growth (Hoagland and Arnon, 1938 Circ. Calif. Agric. Exp. Stat. 347:32, Wickremesinhe and Arteca, 1994 Plant Sci. 101:125–135), however, rooting initiation under complete nutrient minus aqueous mileau has not come into knowledge hitherto. The patent hitherto (Driver, U.S. Pat. No. 4,612,725 dated Sep. 23, 1986; Wochok et al. U.S. Pat. No. 4,478,000 dated Oct. 23, 1984; Dobres et al U.S. Pat. No. 5,843,782 dated Dec. 1, 1998; Nishigori JP 7222536 dated Aug. 22, 1995) do not cover in vitro Rooting Induction (nodal and internodal) under the specified nutrient free conditions. The patent literature for plants in general and mints in particular lacks the method of rapid and direct induction of roots in stems, stem segments, multiple shoots etc. under complete nutrient free aqueous conditions invented herein. The 'aerial roots' have not been produced and represent a new phenomenon of their induction through the invented process of treatment in mint species.

The invented protocol does not require special chemicals, hormones, micro organisms etc. for induction of rooting in stem, twigs or stem segments of Mentha species (*Mentha citrata, Mentha piperita, Mentha cardiaca, Mentha spicata, Mentha arvensis, Mentha virdis, Mentha pulegium,* and *Mentha longifolia*. The roots obtained by the invented protocol are genetically native and physiologically normal.

The method also provides a way to avoid exposure of the plant or plant part to numerous chemicals essentially supplemented in tissue culture media or nutrient solutions or other recipes/formulations of combinations of chemicals and hormones for bringing about rooting in vitro.

The invention is not only economically inexpensive but also technically feasible to be accomplished as and when desired with minimal infrastructural prerequisites. As a synergistic utility, the 'above the ground' canopy of the plants, besides the underground suckers, can be processed through the invented mode to produce rooted propagules to serve as plantlets for the new crop plantation. These propagules possess better and faster establishment behaviour to rapidly resume normal growth thereby offering agronomic advantage. Compared to 18 to 30 days required for sprouting of planted suckers, the root initiation in stem segments by the invention becomes visible within a week.

The juvenile roots could be particularly useful for the specialized physiological and biochemical studies concerning root-shoot interactions, ion uptakes and metabolic precursor feeding and transformations etc.

Additionally, it provides a way of producing rooting in tissue culture raised multiple shoots, required in biotechnological research as well as field transfer of the culture generated variants, clones, transformants etc.

OBJECTS OF THE INVENTION

The main object of the invention is to provide a process for the induction of normal rooting on nodal and internodal stem segments without using hormones and/or other chemical treatments in Mentha species which obviates the drawbacks of the earlier processes as detailed above.

Another object of the invention is to provide a new and easy system of rapid and production of normal roots in stem cuttings of Mentha species thereby leading to large scale production of propagule ready for the field plantation.

Still another object of the invention is producing aerial roots at the non-submerged inter-nodes of the twigs of Mentha species dipped in water under specified conditions.

SUMMARY OF THE INVENTION

In accordance with the above objectives, the invention provides a process for the induction of normal rooting on nodal and internodal stem segments without using hormones and/or other chemical treatments in Mentha species which comprises oblique excision of shoots of Mentha species from the plants, immediately dipping the cut end of twigs or stems into water and keeping in complete dark for up to one week with by varying the temperature cycle for each set of 24 hours duration of the treatment.

DETAILED DESCRIPTION OF THE INVENTION

The invention discloses a process for the induction of normal roots on nodes and internodes of stem segments without using hormones and/or other chemical treatments in Mentha species. Mentha species, constitute not only the major essential oil crop of the global significance but also serves as some of the chief culinary herbs. The present invention is directed to, inter alia, a method of rapid ab initio induction of roots on the nodes and internodes of various Mentha species under nutrient as well as hormone minus aqueous system. The invented process involves applying specified duration of light and or dark treatments with temperature limit. The method allows use of above the ground canopy, of the mints to utilize as propagules for the fresh plantation using the rooted plantlets so generated. The invention provides a method to avoid exposure of the plant or plant parts to various chemicals essentially supplemented in tissue culture media or nutrient solutions or other recipes/formulations. The invention also provides a method of producing rooting in tissue culture raised multiple shoots, required in biotechnological research as well as field transfer of the culture generated variants, clones, transformants etc. and micropropagation purposes. Even 'aerial roots' have also been produced as one of the facets of the invention. The invented process is a novel, fast convenient and inexpensive process for the induction of normal rooting in shoots, stems, twigs or stem segments as well as in tissue culture generated multiple shoots of Mentha species together with successful transplantation of the rooted plantlets for the new crop. A conceptual scientific explanation for the phenomena is proposed.

Accordingly, the present invention provides a process for the induction of normal rooting on nodal and internodal stem segments without using hormones and/or other chemical treatments in Mentha species which comprises oblique excision of shoots of Mentha species from the plants, immediately dipping the cut end of twigs or stems (with at least a pair of leaves) into water and keeping in complete dark for up to one week with temperature cycles of a range of 11–25° C. for 11 hours and of a range of 5–10° C. for 13 hours for each set of 24 hours duration of the treatment.

In an embodiment of the present invention the inflorescence head should be removed from the flowering twigs or shoots.

In another embodiment of the present invention the presence of a pair of leaves on the stem, stem segments, multiple shoots and twigs is mandatory for the induction of rooting In yet another embodiment of the invention the source stems, shoots, twigs, stem segments etc. may be from the native plants growing in soil or from those produced in vitro through tissue culture techniques.

In yet another embodiment of the invention similar root induction may be achieved in certain other plants similar to mints like other Lamiacea, Bacopa monnieri etc.

In yet another embodiment of the invention the water may be replaced once or more times depending upon the rate of achieving root induction, leaching of terpenoidal constituents from the leaves or their putrefaction under water under certain circumstances (anaerobiosis etc.) could lessen or prevent rooting induction. However, aeration or replacement with fresh water could overcome the problem.

A light and dark dependent quantitative as well as qualitative differences in the rooting efficiency and rooting type phenomenon were observed with faster and more abundant rooting under complete dark treatment. As a phenomenally original observation out of the invention the root induction at even the non-submerged internodes (called herein as 'aerial rooting') in the stems or twigs with cut ends dipped in the water was observed only in the case of complete dark treatment.

Scientifically, the mandatory requirement of a pair of leaves for the induction of rooting may be because of their role in catering to the need of carbon and other nutrient to sustain the root growth. As such, it appears that the presence of a pair of leaves holds the secret of signal of rooting initiation with their subsequent role of the nutritional feeding of the initiated roots coming into picture subsequently. The fast and more abundant rooting in dark may be perceived along the same lines as dark treatment could set in the breakdown of storage or reserve starch in the leaves with the soluble carbohydrates thus generated provide abundant supply pool for translocation to the sink of rooting site. Again light-dark cycles could though periodically regulate the balance of starch-soluble carbohydrate production with the mobilization of starch during the intermittent dark period and replenishment of starch pool through photosynthetically generated transitory starch during the light period. It should imply that though rooting initiation and proliferation in light-dark cycles may be slower in rate, it may be temporally more sustainable under the no nutrient medium utilized in the invented process. A support to the above conceptual notion may be drawn from the fact that subterranean (underground) suckers which sprout to give full plants in conventional cultivation of propagation of the mints are thickened ('rhizomatic') stolons having plenty of stored food to sustain sprouting (differentiation) and support early growth of the plantlets just like seed reserves do to the germinating embryos or like potato tuber portion do to the planted potato eyes. As concerns 'aerial roots' induced under complete dark treatment of the invented process, a plausible explanation being postulated herewith is that such roots may be induced under severe depletion of nutrients (which are little available from the water as it is nutritionally un-supplemented and leaves progressively loose their status of higher gradient with progressive supply but no replenishment). Accordingly they may possess some special attribute to take up nutrients from air. It may be something like reminicient of the hanging roots in certain Ficus trees in nature. However, the concept speculated herewith needs experimental scrutiny of acceptance or rejection.

The following examples are given by way of illustration of the present invention and should not be construed to limit the scope of the present invention.

EXAMPLE 1

Twigs of *Mentha arvensis* were harvested from the field crop of *Mentha arvensis* cultivar Kalka growing at the experimental farm of CIMAP. The twigs were kept in tap water in a beaker with the cut ends of the twigs or shoots dipped in water and was given a treatment of cycles of 11 hours of light followed by dark period of 13 hours treatment. In another set the samples were subjected to complete dark treatment. The temperature regime of the treatments was 5 to 10° C. for 13 hours and 14 to 23° C. for 11 hours. Initiation of rooting was observed abundantly at nodes and relatively scantly at internodes by third day of the treatments. By tenth day very elongated and extensive roots with roots hairs were visualized. The rooted plants were transferred to pots. The plants established with 100% survival and exhibited normal growth. No 'aerial roots' (roots appearing on those nodes which are not submerged in water) were observed in stems or twigs subjected to light-dark cycled treatment while they were induced in the case of complete dark treatment. Stems or stem segments with only one leaf or those with no leaf did not produce the roots.

EXAMPLE 2

Twigs of *Mentha cardiaca* were harvested from the field crop of *Mentha cardiaca*, cultivar MCAS-2, growing at the experimental farm of CIMAP. The twigs were kept in water in a beaker with the cut ends of the twigs or shoots dipped in water and were given a treatment of cycles of 11 hours of light followed by dark period of 13 hours treatment. In another set the samples were subjected to complete dark treatment. The temperature regime of the treatments was 5 to 10° C. for 13 hours and 14 to 23° C. for 11 hours. Initiation of rooting was observed abundantly at nodes and scantly at even internodes by third day of the treatment. By tenth day very elongated and extensive roots with roots hairs were visualized. The rooted plants were transferred to pots. The plants established with 100% survival and exhibited normal growth. No 'aerial roots' were observed in stems or twigs subjected to light-dark cycled treatment while 'aerial roots' were induced on all the non-submerged nodes. Stems with only one leaf or those with no leaf did not produce the roots.

EXAMPLE 3

Twigs of *Mentha virdis* were harvested from the field crop of a commercial cultivar of *Mentha virdis* growing at the experimental farm of CIMPA. The twigs were kept in water in a beaker with the cut ends of the twigs or shoots dipped in water and was given a treatment of cycles of 11 hours light followed by dark period of 13 hours treatment. In another set of samples were subjected to complete dark treatment. The temperature regime of the treatments was 8 to 10° C. for 13 hours and 18 to 25° C. for 11 hours. Root initiation was clearly visible as two small roots at each submerged node within 40 hours of start of the treatment under dark while no roots were visible by then in the light-dark cycled treatment. By 72 hours roots started appearing in the light-dark cycled treatment. By tenth day very elongated and extensive roots with roots hairs were visualized. The root plants were transferred to pots. The plants established with 100% survival and exhibited normal growth.

EXAMPLE 4

Twigs of *Mentha arvensis* were harvested from the field crop of *Mentha arvensis*, cultivar Kalka, growing at the experimental farm of CIMAP. The twigs were kept in distilled water in a beaker with the cut ends of the twigs or shoots dipped in water and was given a treatment of cycles of 11 hours light followed by dark period of 13 hours treatment. In another set the samples were subjected to complete dark treatment. The temperature regime of the treatments was 8 to 10° C. for 13 hours and 18 to 25° C. for 11 hours. After 5 days, two induced roots from each node with up to 4–5 mm length were observed in case of light-dark cycled treatment while the roots produced in case of dark treatment were more elongated (7 mm). The rooted plants were transferred to pots. The plants established with 100% survival and exhibited normal growth.

EXAMPLE 5

Twigs of *Mentha spicata* were harvested from the field crop of *Mentha spicata*, cultivar MSS-5, growing at the experimental farm of CIMAP. The twigs were kept in water in a beaker with the cut ends of the twigs or shoots dipped in water and was given a treatment of cycles of 11 hours light followed by dark period of 13 hours treatment. In another set the samples were subjected to complete dark treatment. The temperature regime of the treatments was 8 to 10° C. for 13 hours and 18 to 25° C. for 11 hours. After 5 days, one to two roots (5–12 mm) from each node were observed in case of light-dark cycled treatment while the roots produced in case of dark treatment were observed at nodes (2 to 3 roots at each node, 7 to 18 mm in length) as well as at internodes (one to two roots at each submerged internode, up to 2 mm in length). The rooted plants were transferred to pots. The plants established with 100% survival and exhibited normal growth.

EXAMPLE 6

Twigs of *Mentha piperita* were harvested from the field crop of *Mentha piperita,* cultivar Kukrail, growing at the experimental farm of CIMAP. The twigs were kept in water in a beaker with the cut ends of the twigs or shoots dipped in water and was given a treatment of cycles of 11 hours of light followed by dark period of 13 hours treatment. In another set the samples were subjected to complete dark treatment. The temperature regime of the treatments was 8 to 10° C. for 13 hours and 18 to 25° C. for 11 hours. By fifth day one to two roots (6–15 mm) from each node were observed in case of light-dark cycled treatment while the roots produced in case of dark treatment were observed to be 2 to 3 in number with root length in the range of 4 to 25 mm at nodes as well as internodes. The rooted stems or stem parts were transferred to pots. The plants established with 100% survival and exhibited normal growth.

EXAMPLE 7

Twigs of *Mentha pulegium* were harvested from the field crop of a commercial cultivar of *Mentha pulegium* growing at the experimental farm of CIMAP. The twigs were kept in water in a beaker with the cut ends of the twigs or shoots dipped in water and was given a treatment of cycles of 11 hours of light follows by dark period of 13 hours treatment. In another set of samples were subjected to complete dark treatment. The temperature regime of the treatments was 8 to 10° C. for 13 hours and 18 to 25° C. for 11 hours. The roots became visible within 48 hours of the treatments with one roots per node in case of dark treatment and but no response in the light-dark cycled treatment. However, by fifth day roots were visible in both the cases at all the submerged nodes with root lengths measuring only up to 0.5 mm in case of cycled light-dark treatment but longer (2 mm) in case of complete dark treatment. The rooted stems or stem parts were transferred to pots. The plants established with 100% survival and exhibited normal growth.

EXAMPLE 8

Twigs of *Mentha cardiaca* were harvested from the field crop of *Mentha cardiaca*, cultivar MCAS-2, growing at the experimental farm of CIMAP. The twigs were kept in distilled water in a beaker with the cut ends of the twigs or shoots dipped in water and was given a treatment of cycles of 11 hours of light followed by dark period of 13 hours treatment. In another set the samples were subjected to complete dark treatment. The temperature regime of the treatments was 8 to 10° C. for 13 hours and 18 to 25° C. for 11 hours. The roots became visible within 48 hours of the treatments with at least two roots per node in case of dark treatment and but no response in the light-dark cycled treatment. However by fifth day roots were visible in both the types of treatments. Numerically, there was only one root per node in case of the light-dark cycled treatment whereas their number was more (2 to 4) in case of the complete dark treatment with the roots appearing both at nodes as well as internodes. The rooted stems or stem parts were transferred to pots. The plants established with 100% survival and exhibited normal growth.

EXAMPLE 9

Twigs of *Mentha citrata* were harvested from the field crop of *Mentha citrata*, cultivar Kiran, growing at the experimental farm of CIMAP. The twigs were kept in water in a beaker with the cut ends of the twigs or shoots dipped in water and were given a treatment of cycles of 11 hours of light followed by dark period of 13 hours treatment. In another set the samples were subjected to complete dark treatment. The temperature regime of the treatments was 8 to 10° C. for 13 hours and 18 to 25° C. for 11 hours. The roots became visible within 48 hours of the treatments both in case of dark treatment as well as the light-dark cycled treatment but the roots (two number per node) were much longer in length in dark than in the light-dark treatment. By fifth day the number of roots per node remained the same roots in the later case with length reaching up to 25 mm whilst in case of the former treatment their number enhanced up to 4 per node with length reaching up to 35 mm. Internodal roots were also induced in both the treatments. The rooted stems or stem parts were transferred to pots. The plants established with 100% survival and exhibited normal growth.

EXAMPLE 10

Twigs of *Mentha arvensis* were harvested from the field crop of *Mentha arvensis*, cultivar Kalka, growing at the experimental farm of CIMAP. The twigs were kept in water in a beaker with the cut ends of the twigs or shoots dipped in water and were given a treatment of cycles of 13 hours of light followed by dark period of 11 hours treatment. In another set the samples were subjected to complete dark treatment. The temperature regime of the treatments was 10° C. for 11 hours and 20 to 25° C. for 13 hours. The roots became visible by sixth day but only under dark treatment. Also, rapidly growing internodal roots were also induced in both the treatments. The rooted stems or stem parts were transferred to pots. The plants established with 100% survival and exhibited normal growth.

EXAMPLE 11

Twigs of *Mentha arvensis* were harvested from the field crop of *Mentha arvensis*, cultivar Kalka, growing at the experimental farm of CIMAP. The twigs were kept in distilled water a beaker with the cut ends of the twigs or shoots dipped in water and subjected to complete dark treatment with either a temperature regime of 10° C. for 11 hours and 20 to 25° C. for 13 hours of 8 to 10° C. throughout. Roots were induced at nodes as well as internodes were 24 hours in case of dark treatment involving the temperature regimes of 10° C. for 11 hours and 20 to 25° C. for 11 hours with no response in the treatment involving the lower temperature of 8 to 10° C. throughout.

EXAMPLE 12

Twigs (both those bearing flowering heads as well as those with no inflorescence) of *Mentha arvensis* were harvested from the field crop of *Mentha arvensis,* cultivar Kalka, growing at the experimental farm of CIMAP. The twigs were kept in three sets (including non-flowering twigs, flowering twigs and flowering twigs with inflorescence removed) water in separate beakers with the cut ends of the twigs or shoots dipped in water and subjected to complete dark treatment with a temperature regime of the treatments was 10° C. for 13 hours and 15 to 24° C. for 11 hours. By fifth day, nodal roots got induced in the twigs lacking inflorescence ab initio as well as in twigs with inflorescence removed before treatment but no root-induction response was found in the flowering shoots subjected to the treatment as such.

EXAMPLE 13

Twigs of *Mentha arvensis* were harvested from the field crop of *Mentha arvensis,* cultivar Kalka, growing at the experimental farm of CIMAP. The twigs were kept in distilled water in a test tube with the cut ends of the twigs or shoots dipped in water and were given a complete dark with the temperature regime of the treatments was 5 to 10° C. for 13 hours and 14 to 23° C. for 11 hours. In another set, the twigs were kept under identical conditions except that the water was supplemented with antibiotic Sporidex at a concentration of 500 µg per ml (to prevent any chance of bacterial infection) with weekly changing of the treatment water. Rooting induction was observed within a week in both the control as well as Sporidex treatment.

EXAMPLE 14

Multiple shoots of *Mentha arvensis* were generated through standard tissue culture techniques using MS medium supplemented with 3 mg/l BAP and 1 mg/l IAA using shoot tip as ex-plant. Multiple shoot formation occurred in about four to five weeks. The multiple shoots with very young and tender leaves were excised to induce roots through the invented process in total dark as above. Rooting was induced by fifth day of the treatment.

EXAMPLE 15

*Mentha arvensis* shoots were excised from the field grown crop maintained for the commercial sucker production. The stem segments with one or more nodes were kept on a plastic strainer in such a way that the parts of the shoots remain in contact with the water contained down in the vessel. The assembly was kept in total dark with the temperature regime described in Example 1. Rooted plantlets were produced within five days and were transplanted to field as propagules for the new crop. The plants were established with 100% success and displayed normal growth behaviour.

Following is a tabulated account of the in vitro root induction response in Mentha species in aqueous system free from hormones, nutrients and other chemicals.

| Treatment | Normal Root Induction | "Aerial Root" Induction |
|---|---|---|
| Complete Dark | Yes [fast, more in number] | Yes |
| Light-Dark Cycles | Yes [slow in response and growth, less in number] | No |

The main advantages of the present invention are
1. The invented protocol does not require specialty chemicals, hormones, microorganisms etc. for induction of rooting in shoots of mints.
2. The roots obtained are genetically native and physiologically normal. Thereby, all observations derived from them would mean truly discerning the characteristic of roots of the plant species under reference.
3. The invention is not only economically inexpensive but also technically feasible to be accomplished as and when desired with minimal infrastructural prerequisite.
4. The invention provides a way to avoid exposure of the plant or plant part to numerous chemicals essentially supplemented in tissue culture media or nutrient solutions or other recipes/formulations
5. The invention also provides a way of producing rooting in tissue culture raised multiple shoots, required in biotechnological research as well as field transfer of the culture generated variants, clones, transformants etc.
6. As a synergistic utility, the 'above the ground' canopy of the plants, besides the underground plant the suckers, can be processed through the invented mode to produce rooted propagules to serve as plantlets for the new crop plantation.
7. The pre-rooted stems or stem segments possess better and faster establishment behaviour to rapidly resume normal growth thus offering agronomic advantage.
8. Compared to 18 to 30 days required for sprouting of planted suckers, the rooting initiation in stems or stem segments by the invention becomes visible within a week.
9. The invention also provides a convenient and simple system of getting normal roots for biochemical studies for the root metabolic studies including root-shoot interactions in the species.
10. The juvenile roots produced on the twigs or stems by the invented process could be particularly useful for the specialized physiological and biochemical studies concerning ion uptakes and metabolic precursor feeding and transformations etc.
11. Getting roots in almost zero state aqueous micromileau, the uptake mechanisms and their modulations can be dissected more discretely.
12. The aerial roots obtained with the invented process form a unique and novel rooting phenomenon deserving examination of their functional relevance which may eventually even be new one in entirety for the mints.

What is claimed is:

1. A process for the induction of normal rooting on nodal and internodal stem segments without using hormones or other chemical treatment in Mentha species, which comprises oblique excision of shoots of Mentha species from the plants, immediately dipping the cut end of twigs or stems having at least one pair of leaves into water and keeping in complete dark for up to one week with temperature cycles of a range of 11–25° C. for 11 hours and of a range of 5–10° C. for 13 hours for each set of 24 hours duration of the treatment whereby roots are formed.

2. A process as claimed in claim 1 wherein an inflorescence head is removed from flowering twigs or shoots.

3. A process as claimed in claim 1 wherein the stem, stem segments, multiple shoots and twigs used for the induction of rooting comprise a pair of leaves.

4. A process as claimed in claim 1 wherein source stems, shoots, twigs, and stem segments are selected from plants growing in soil or plants produced in vitro through tissue culture techniques.

5. A process as claimed in claim 1 wherein the water may be replaced one or more times.

6. A process for induction of normal rooting on nodal and internodal stem segments without using hormones or other chemical treatment in Lamiaceae, Bacopa monnieri, or Mentha species, which comprises oblique excision of shoots from the plants, immediately dipping the cut end of twigs or stems having at least one pair of leaves into water and keeping in complete dark for up to one week with temperature cycles of a range of 11–25° C. for 11 hours and a range of 5–10° C. for 13 hours for each of 24 hours duration of the treatment whereby roots are formed.

7. A process as claimed in claim 6 wherein an inflorescence head is removed from flowering twigs or shoots.

8. A process as claimed in claim 6 wherein stems, stem segments, multiple shoots or twigs used for the induction of rooting comprise a pair of leaves.

9. A process as claimed in claim 6 wherein the source stems, shoots, twigs, stem segments are selected from plants growing in soil or plants produced in vitro through tissue culture techniques.

10. A process as claimed in claim 6 wherein the water may be replaced one or more times.

11. A process for induction of normal rooting on nodal and internodal stem segments without using hormones or other chemical treatment in Lamiaceae, Bacopa monnieri, or Mentha species, which comprises oblique excision of shoots from the plants, immediately dipping the cut end of twigs or stems having at least one pair of leaves into nutrient-free water and keeping in complete dark for up to one week with temperature cycles of a range of 11–25° C. for 11 hours and a range of 5–10° C. for 13 hours for each of 24 hours duration of the treatment.

12. A process for induction of normal rooting on nodal and internodal stem segments without using hormones or other chemical treatment in Lamiaceae, Bacopa monnieri, or Mentha species, which comprises oblique excision of shoots from the plants, immediately dipping the cut end of twigs or stems having at least one pair of leaves into nutrient-free water and keeping in complete dark for up to one week with temperature cycles of a range of 11–25° C. for 11 hours and a range of 5–10° C. for 13 hours for each of 24 hours duration of the treatment to induce aerial rooting.

13. A process for induction of normal rooting on nodal and internodal stem segments without using hormones or other chemical treatment in Lamiaceae, Bacopa monnieri, or Mentha species, which comprises oblique excision of shoots from the plants, immediately dipping the cut end of twigs or stems having at least one pair of leaves thereon into nutrient-free water and keeping in complete dark for up to one week with temperature cycles of a range of 11–25° C. for 11 hours and a range of 5–10° C. for 13 hours for each of 24 hours duration of the treatment to effect root induction.

* * * * *